United States Patent [19]

Tenjinbayashi

[11] Patent Number: 4,871,255
[45] Date of Patent: Oct. 3, 1989

[54] OPTICAL NONDESTRUCTIVE TESTING METHOD OF COMPOSITE MATERIALS

[75] Inventor: Koji Tenjinbayashi, Tsukuba, Japan

[73] Assignees: Agency of Industrial Science & Technology; Ministry of International Trade & Industry, both of Tokyo, Japan

[21] Appl. No.: 174,430

[22] Filed: Mar. 28, 1988

[30] Foreign Application Priority Data

Apr. 17, 1987 [JP] Japan ................................. 62-96020

[51] Int. Cl.$^4$ .............................................. G01B 9/02
[52] U.S. Cl. .................................... 356/354; 356/360; 73/656
[58] Field of Search .................. 356/354, 360; 73/655, 73/656

[56] References Cited

U.S. PATENT DOCUMENTS 3,899,921 8/1975 Hockley ................................. 73/656

Primary Examiner—Vincent P. McGraw
Assistant Examiner—S. A. Turner
Attorney, Agent, or Firm—Oblon, Spivak, McClelland, Maier & Neustadt

[57] ABSTRACT

An optical nondestructive testing method of composite materials utilizes optical interferometry to find the resonant vibration from at least one surface of the target part of an object being inspected, and also determines the resonant frequency at that time. Another resonant frequency exhibiting the same resonant vibration is then obtained from the rear surface of the part of the object being inspected and the two resonant frequencies are used to derive the depth of defects in the object.

4 Claims, 4 Drawing Sheets

OPTICAL NONDESTRUCTIVE TESTING METHOD OF COMPOSITE MATERIALS

BACKGROUND OF THE INVENTION

1. Field of the Invention

This invention relates to an optical nondestructive testing method of composite materials, and in particular to an optical nondestructive testing method of laminate-structure composite materials.

2. Prior Art Statement

A composite material is a material that is obtained by uniting two or more materials or two or more layers by some physical or chemical method. Compared to simple materials, composite materials have excellent lightness and strength, and because of this composite materials have recently come into use as construction materials for aircraft and the like.

However, any internal defect, such as a disbond, for example, causes a loss of the properties of the composite material, which in the case of an aircraft application, for example, could result in a major accident. This being the case, nondestructive testing of composite materials is of major importance.

Optical interferometry is one of the known optical nondestructive testing methods of composite materials. In optical interferometry, the composite material is vibration stressed and holographic or speckle pattern interferometry is used to find the shape of a disbond from the resonance mode of the disbond site.

L. A. Kevsch, for example, has pointed out that when the shape of a disbond is a circle (of radius r), the depth d of the disbond with respect to resonant frequency f is $f = kd/r^2$ (p. 306 Holographic Nondestructive Testing edited by R. K. Erf, Academic Press (1974)). Here, constant k is $k = \beta, \sqrt{[E/3\rho(1-V^2)]}, \beta$ is a constant decided according to the resonance mode, E is the Young's modulus, $\rho$ is density and V is Poisson's ratio.

Conventional optical testing methods enable the shape of disbonds and other such defects in composite materials to be found, but because the usual objective was the shape of a defect, it was not possible to ascertain the depthwise location of the defect in the material. In order to repair defects in composite materials it is necessary to know the depth at which the defect is located as well as its shape. As such, there has been a demand for the development of a testing technique that would enable both the shape and the depth of a disbond or other such defect in a composite material to be found.

OBJECT AND SUMMARY OF THE INVENTION

An object of this invention is to provide an optical nondestructive testing method of a composite material which enables the shape and the depthwise location of defects in the material to be accurately determined.

For attaining the aforesaid object the present invention provides an optical nondestructive testing method of composite materials comprising the use of optical interferometry to obtain the resonant vibration mode on at least one surface of the target part of the object being inspected; determining also the resonant frequency at that time; obtaining another resonant frequency exhibiting the same resonant vibration mode from the rear surface of the part of the object being inspected; and using the two said resonant frequencies to calculate the position of the defect in the thickness direction of the part of the object being inspected.

As thus described in the foregoing, in accordance with this invention whereby a specimen is frequency scanned while being subjected to vibration stressing, the shape of the disbond can be determined from the shape of the interference fringe pattern in the resonance mode resulting from observations of the disbond region taken from both sides of the specimen in the same resonance mode, while the depth of the disbond can be determined from the respective resonant frequency values obtained from each surface.

When the resonant frequency cannot be measured from the rear surface, a material which is the same as that of the inspection object is affixed to the surface at the region to be inspected and the resonant frequency thereof is measured. With the optical nondestructive testing method of composite materials according to this invention, the depthwise location of a disbond can be readily ascertained, even when the value of the material constant is not known and regardless also of the shape of the disbond.

The above and other objects and features of the invention will become more apparent from the following detailed description with reference to the accompanying drawings.

DETAILED DESCRIPTION OF THE PREFERRED EMBODIMENTS

Figure 1:
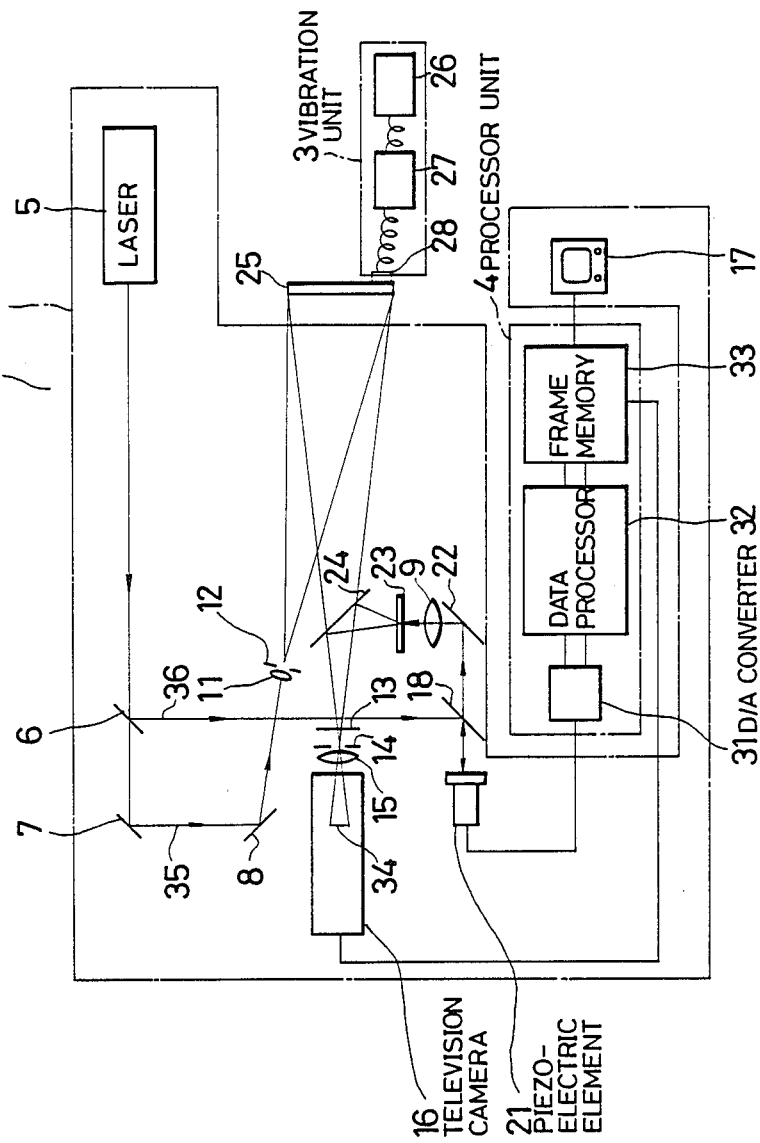
FIG. 1 is an explanatory schematic view of an example of a nondestructive test apparatus according to a first embodiment of the invention.
Figure 2:
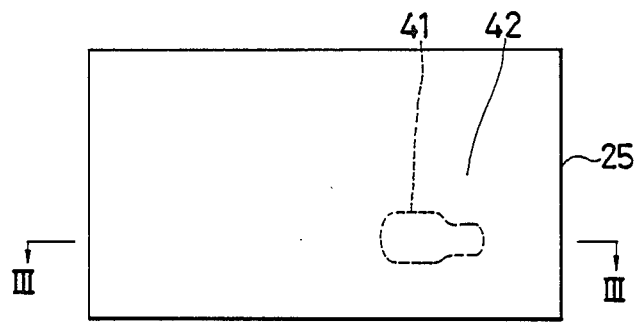
FIG. 2 is an explanatory plan view of an object to be inspected.

FIG. 1 is a schematic view showing an example of the general arrangement of an optical nondestructive test apparatus 1 for testing composite materials, according to this invention. The nondestructive test apparatus 1 is constituted of an interferometer 2, a vibration unit 3 and a processor unit 4. The interferometer 2 is provided with a laser light source 5, a beam splitter 6, a mirror 7, a mirror 8, a lens 9, a lens 11, a pinhole 12, a polarizing plate 13, an aperture 14, a lens 15, a television camera 16, a display monitor 17, a beam splitter 18, a piezo-electric element 21, a mirror 22, a diffuser plate 23 and a semi-transparent mirror 24.

The vibration unit 3 is for applying vibrations to the inspection object 25 of a composite material, and is provided with a vibration generator system 26, an amplifier 27 and a vibrator 28.

The processor unit 4 is provided with a D/A converter 31, a processor 32 and a frame memory 33. Optical nondestructive inspection of composite materials using the nondestructive test apparatus 1 of the above construction will now be described.

To begin with, the vibrator 28 is attached to the inspection object 25 and the inspection object 25 is vibrated by vibrations generated by the vibration generator system 26. Whether or not the composite material used as the inspection object 25 for testing by the present invention has a black surface like carbon fiber, or is flat in shape, or large, the principle remains the same. In the case of a composite material that is constituted of multiple layers, although there is no limitation on the number of layers, as the size of the vibrating force required is dependent on the thickness of the material, the amount of vibrating force needed increases with the increase in the number of layers. Also, the method of the present invention does not allow determination of the depthwise location of a defect in the case of a five-layer composite material, for example, in which the material of each layer is different. However, in the case of a composite material constituted of one hundred layers of just two types of material arranged in strict alternation, it would be possible to determine the depth of a defect because on an overall basis the material can be regarded as being more or less uniform in nature. In addition, when a large area is to be inspected at one time it is necessary to use a laser light source that has a high output and long-range coherence, such as an argon ion laser, for example. Large objects such as ships or aircraft which are difficult to inspect at one time have to be divided up into smaller areas and the inspection carried out over a number of occasions.

The frequency of the vibration to be applied to the composite material ranges from several kilohertz up to around 100 kilohertz, depending on the nature of the material and its structure, size and thickness. The higher the frequency, the smaller the defect that can be detected. Also, the larger the vibration force, the deeper the level at which defects can be detected.

A laser beam emitted from the laser light source 5 is divided by the beam splitter 6 into two beams 35, 36. The path of one laser beam 35 is deflected by mirror 7 and mirror 8, passes through the lens 11 and the pinhole 12, whereby it is changed to a divergent beam and illuminates the surface of the target portion of the inspection object 25. The beam 35 is reflected from the target portion and impinges on the screen surface 34 of the television camera 16. The beam impinging on the screen surface 34 is modulated by the vibrating surface of the target portion.

The laser beam may be of any wavelength that can be picked up by the television camera. Also, a filter may be disposed in front of the television camera that only passes light of the laser beam wavelength, so that even if other light is included, the inspection can proceed without being affected by such other light.

The other laser beam 36 produced by the division of the original laser beam by the beam splitter 6 is reflected by the beam splitter 18 and then by a reflecting face (not shown) provided on the piezo-electric element 21 and passes through the beam splitter 18, is deflected by the mirror 22, diffused by the lens 9 and the diffuser plate 23, reflected by the semi-transparent mirror 24 and impinges on the screen surface 34 of the television camera 16. The piezo-electric element 21 produces a phase shift in the laser beam 36.

The two beams 35 and 36 produce an interference pattern on the screen surface 34 of the television camera 16. Three interference wavefronts of the beam 36 phase-shifted by the piezo-electric element 21, i.e., an interference wavefront when the piezo-electric element was not moved, an interference wavefront when the piezoelectric element was moved forward, and an interference wavefront when the piezo-electric element was moved rearward, are stored in the frame memory 33. Computing these using the processor 32 enables electronic speckle pattern interferometry to be utilized and provides an interference fringe pattern that shows the vibrational state of the inspection object 25. The shape of a defect in the target portion of the inspection object 25 can be determined directly from the shape of the interference fringe pattern. The depthwise location of the defect can be determined by observing the shape of the interference fringe pattern on the display monitor 17 and specifying the vibration mode (m, n), such as, for example, nodal line (m, n: 0, 2) or nodal circle (m, n: 1, 0). The resonant frequency $fn_1$ in this specified vibration mode is then input into the processor 32.

Figure 3:
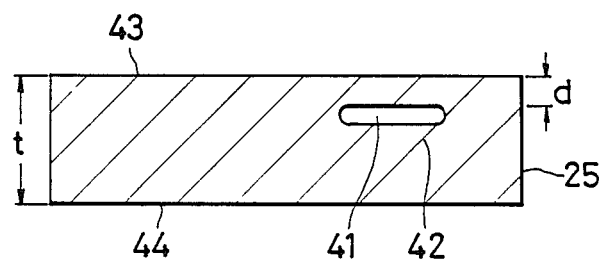
FIG. 3 is a cross-sectional view along line III—III of FIG. 2.

The inspection object 25 is then turned over to carry out measurements from the rear surface of the inspection object 25. A resonant frequency $fn_2$ in the same specific vibration mode is obtained and input into the processor 32. The depth of the defect is then determined from the two resonant frequencies $fn_1$ and $fn_2$ by the following calculation performed by the processor 32. If the defect 41 is assumed to be at a depth d below the upper surface 43 of the portion being inspected 42, as shown in FIG. 3, the resonant frequency $fn_1$ of the upper surface 43 and the resonant frequency $fn_2$ of the lower surface 44 can be represented by the following equations.

$$fn_1 = K\{d/F(\text{area})\} \quad (1)$$

$$fn_2 = K(t-d)/F(\text{area}) \quad (2)$$

From equations (1) and (2), $$d = t/\{1 + (fn_2/fn_1)\} \quad (3)$$

Here, F(area) is a function that depends on the shape of the defect; K is a constant that is decided according to the shape of the defect and the material; and t is the thickness of the material.

Thus, as is clear from the equation (3), the depth d at which the defect 41 is located can be determined from just the thickness t of the inspection object 25 and the resonant frequencies $fn_1$ and $fn_2$.

Figure 4:
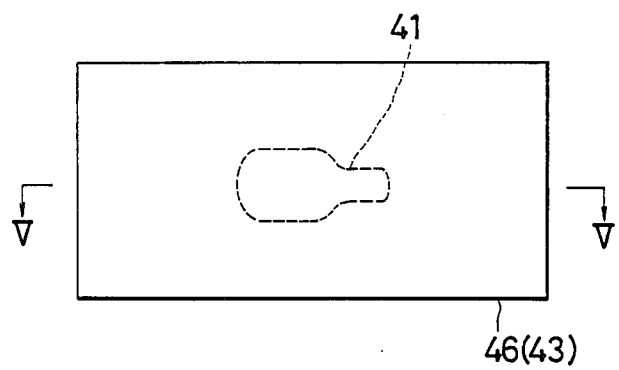
FIG. 4 is an explanatory plan view of another example of an object to be inspected.
Figure 5:
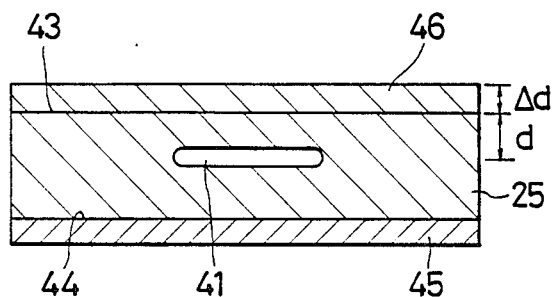
FIG. 5 is a cross-sectional view along line V—V of FIG. 4.

Next, as illustrated in FIGS. 4 and 5, when an object 45 is affixed to the inspection object 25 and measurements cannot be performed from the rear surface 44 of the inspection object 25, after the resonant frequency $fn_1$ has been found by measurements made from the front surface 43 of the inspection object 25, a panel 46 of a known thickness and constituted of the same material as that of the inspection object 25 is affixed to the front surface 43 and measurements are carried out from the said panel 46 to obtain a resonant frequency $fn_3$.

Thus, in the same way that the resonant frequency $fn_1$ of the upper surface 43 can be represented by equation (1), the resonant frequency $fn_3$ when the panel 46 has been affixed to the upper surface 43 can be represented by the following equation (4).

$$fn_1 = K\{(d/F(\text{area})\} \quad (1)$$

$$fn_3 = K\{(d+\Delta d)/F(\text{area})\} \quad (4)$$

From the equations (1) and (4), the depth d of the defect 41 can therefore be determined as follows.

$$d = \Delta d/\{(fn_3/fn_1) - 1\} \quad (5)$$

Thus, with the optical nondestructive testing method of composite materials according to the present invention in which holographic or speckle pattern interferometry is used to inspect a composite material for disbonds, an inspection object is frequency scanned while being subjected to vibration stressing, and the shape of the disbond is determined from the shape of an interference fringe pattern in the resonance mode resulting from measurement observations of the disbond region taken from both the front and rear surfaces of the inspection object in the same resonance mode, while the depth of the disbond is determined from the resonant frequency values of the two sides. In addition, when observations cannot be made from the rear surface, as a temporary expedient, after measurements from the front surface have been completed, measurements can be carried out by affixing to the front surface a panel of the same material as the front surface thereby to enable the depth of the disbond to be calculated on the basis of changes in the resonant frequency of a fixed resonance mode after the panel is attached compared to before.

Thus, with the optical nondestructive testing method of composite materials according to this invention, the depthwise location of a disbond can be readily known, even if the value of the material constant is not known and the objective is the shape of the disbond.

Figure 6:
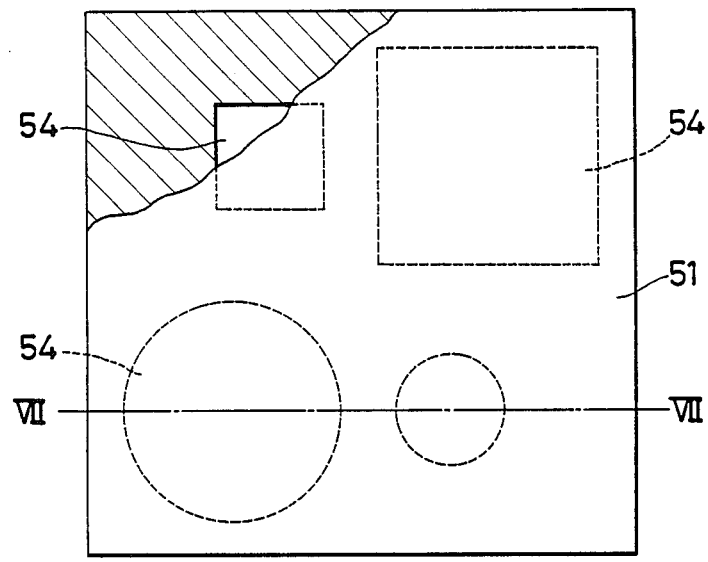
FIG. 6 is a partially cutaway plan view f an object for experimental use.
Figure 7:
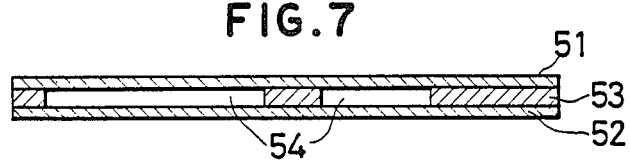
FIG. 7 is a cross-sectional view along line VII—VII of FIG. 6.

Another embodiment of the invention will now be described with reference to FIGS. 6 and 7. An inspection object is comprised of an aluminum plate 53 that is 150 mm square and 1 mm thick. The plate 53 is provided with two square holes, one 60 mm square and the other 30 mm square, and two circles, one 30 mm in diameter and the other 60 mm in diameter. The aluminum plate 53 is sandwiched between a 0.125 mm-thick upper aluminum plate 51 and a 0.254 mm thick lower aluminum plate 55.

In a real composite object for actual use a middle layer would be the same thickness as an adhesive layer. However, because adhesive squeezing out makes it difficult to produce an accurately shaped defect (disbond area), the said square and round holes were formed in the middle layer to act as defects. Here, the depth d of the defect is calculated by equation (6) instead of equation (3).

$$d = 0.379/(1 + fn_2/fn_1) \qquad (6)$$

The vibrator is fastened to the above inspection object, and the object is vibrated by a sine wave produced by a generator and passed through an amplifier. A laser beam from an argon ion laser source (wavelength: 514.5 nm) is divided by a beam splitter. The beam passing through the beam splitter is reflected by a beam reflector, rerouted, and formed into a divergent beam by a microscope object lens and a pinhole, and as the object beam illuminates the inspection object. The other beam that was reflected by the beam splitter is reflected by another beam splitter, and then by a beam reflector provided on a piezo-electric element and is thereby directed back along the original light path. The beam is then deflected by another beam reflector and, after being diverged by a lens, impinges on a diffuser plate as the reference beam. The object beam and reference beam are superposed by a semi-transparent mirror and passed through a polarizing plate and enter a television camera.

The three kind of speckle interference patterns of the reference beam phase-shifted by the piezo-electric element are captured by the televison camera and stored in a frame memory. The amount of phase shift by piezo-electric element is ordered by a minicomputer through a D/A converter. The stored image data are processed by a minicomputer and then appear for the first time as an interference fringe pattern.

In this embodiment, the resonant frequency was obtained as follows. The vibration input was increased to obtain an approximate indication of the resonant frequency, and the vibration input was then reduced with, the frequency left at that setting, until the interference fringe was down to about one band. Usually an interference fringe forms a closed curve, so in that state the frequency was fine-tuned to maximize the area enclosed by the closed curve This was taken to be the resonant frequency.

The following table shows the measured results with respect to the depth of the defects, i.e., the thickness of the upper plate 51a.

|  | No. | | | | | | |
| --- | --- | --- | --- | --- | --- | --- | --- |
|  | 1 | 2 | 3 | 4 | 5 | 6 | 7 |
| Shape of defect | Square | Circle | Circle | Square | Circle | Circle | Square |
| Diameter or Length of side (mm) | 60 | 60 | 60 | 60 | 60 | 30 | 30 |
| Mode (m, n) | (0, 0) | (0, 0) | (0, 1) | (0, 2) | (0, 2) | (0, 0) | (0, 2) |
| Front surface resonant frequency $fn_1$ (Hz) | 330 | 367 | 744 | 980 | 1176 | 1535 | 3983 |
| Rear surface resonant frequency $fn_2$ (Hz) | 653 | 719 | 1592 | 1904 | 2363 | 3085 | 8182 |
| Theoretical value (mm) |  |  |  | 0.125 |  |  |  |
| Measured value (mm) | 0.1272 | 0.1281 | 0.1207 | 0.1288 | 0.1259 | 0.1259 | 0.1241 |
| Mean value (mm) |  |  |  | 0.1258 |  |  |  |
| Mean value error (%) |  |  |  | 0.658 |  |  |  |
| Square mean error (%) |  |  |  | 2.133 |  |  |  |

As the table shows, the measured means square error was an extremely high-precision 2.13% that shows clearly the defect depth measurement capability.

Of course, equation (3) is applicale in place of equation (6). In this case, since the thickness t of the material is 1.379 mm, the depth d of the defect can be obtained from $1.379/\{1 + (fn_2/fn_1)\}$.

What is claimed is:

1. An optical nondestructive testing method of composite materials, comprising the steps of:
   utilizing optical inteferometry to obtain a resonant vibration mode on a front surface of a target part of an object being inspected and also determining resonant frequency at that time;
   then obtaining another resonant frequency exhibiting the same resonant vibration mode from a rear surface of said part of the object being inspected; and using the two said resonant frequencies to derive the position of a defect in a thickness direction of the part of the object being inspected.

2. The optical nondestructive testing method according to claim 1, wherein a position of a defect in a thickness direction is obtained from an equation $d=t/\{+(f_{n2}/f_{n1})\}$ derived from a front surface resonant frequency $f_{n1}$ and a rear surface resonant frequency $f_{n2}$ (t in the equation being the thickness of the inspection object).

3. An optical nondestructive testing method of composite materials, comprising the steps of:
   utilizing optical inteferometry to obtain a resonant vibration mode on at least a front surface of a target part of an object being inspected and also determining resonant frequency at that time;
   obtaining a resonant frequency exhibiting the same resonant vibration more at a panel member constituted of a material that is the same as that of the inspection object and which is affixed to the front surface of the target part of the object being inspected; and
   using the two said resonant frequencies to derive the position of a defect in a thickness direction of the target part of the object being inspected.

4. The optical nondestructive testing method according to claim 3, wherein:
   a position d of a defect in a thickness direction is obtained from an equation $d=\Delta d/\{(f_{n3}/f_{n1})-1\}$ derived from a front surface resonant frequency $f_{n1}$ and a panel surface resonant frequency $f_{n2}$, the $\Delta d$ in the equation being the thickness of said panel member is which is affixed on the target part of the object to be inspected.

* * * * *